(12) United States Patent
Hallinan et al.

(10) Patent No.: US 8,431,740 B2
(45) Date of Patent: Apr. 30, 2013

(54) CONTROLLING DECANTER PHASE SEPARATION OF ACETIC ACID PRODUCTION PROCESS

(75) Inventors: Noel Hallinan, Loveland, OH (US); Michael E. Fitzpatrick, League City, TX (US); John D. Hearn, Beach City, TX (US); Miraj S. Patel, Sugar Land, TX (US)

(73) Assignee: Equistar Chemicals, LP, Houston, TX (US)

( * ) Notice: Subject to any disclaimer, the term of this patent is extended or adjusted under 35 U.S.C. 154(b) by 373 days.

(21) Appl. No.: 12/804,424

(22) Filed: Jul. 21, 2010

(65) Prior Publication Data

US 2012/0022289 A1    Jan. 26, 2012

(51) Int. Cl.
*C07C 51/12* (2006.01)
(52) U.S. Cl.
USPC .......................................................... 562/519
(58) Field of Classification Search .................... 562/519
See application file for complete search history.

(56) References Cited

U.S. PATENT DOCUMENTS

| | | | |
|---|---|---|---|
| 5,817,869 A | 10/1998 | Hinnenkamp et al. | |
| 5,932,764 A | 8/1999 | Morris et al. | |
| 6,103,934 A * | 8/2000 | Hallinan et al. | 562/517 |
| 6,552,221 B1 | 4/2003 | Hallinan et al. | |
| 6,677,480 B2 * | 1/2004 | Huckman et al. | 562/519 |
| 7,208,625 B1 | 4/2007 | Wang et al. | |
| 7,271,293 B2 | 9/2007 | Trueba et al. | |
| 7,345,197 B1 | 3/2008 | Hallinan et al. | |
| 7,485,749 B2 | 2/2009 | Sawyer et al. | |
| 7,524,988 B2 * | 4/2009 | Harris et al. | 562/608 |
| 7,790,919 B2 | 9/2010 | Hallinan et al. | |
| 7,790,920 B2 | 9/2010 | Brtko et al. | |
| 7,812,191 B2 | 10/2010 | Hallinan et al. | |

* cited by examiner

*Primary Examiner* — Joseph Kosack

(57) ABSTRACT

Disclosed is a method for controlling the decanter phase separation of an acetic acid production by methanol carbonylation. The method comprises measuring the methyl acetate concentration of the reactor mixture, calculating the density of the decanter heavy, organic phase according to the measured methyl acetate concentration, and adjusting the conditions in the reactor or in the decanter to ensure phase separation of the decanter.

10 Claims, No Drawings

CONTROLLING DECANTER PHASE SEPARATION OF ACETIC ACID PRODUCTION PROCESS

FIELD OF THE INVENTION

The invention relates to the preparation of acetic acid. More particularly, the invention relates to a method for controlling the decanter phase separation of an acetic acid production process.

BACKGROUND OF THE INVENTION

Process for producing acetic acid by methanol carbonylation involves multiple steps, including reaction, flashing, light-ends distillation, phase separation, heavy-ends distillation, etc. The carbonylation reaction is performed by reacting methanol and carbon monoxide in the presence of a carbonylation catalyst, a catalyst stabilizer, methyl iodide, water and methyl acetate to produce an acetic acid stream comprising the catalyst, the catalyst stabilizer, methyl iodide, methyl acetate, water, and acetic acid. The acetic acid stream is flashed to produce a vapor stream comprising acetic acid, water, methyl acetate, methyl iodide and acetaldehyde, and a liquid stream comprising the catalyst and the catalyst stabilizer. The vapor stream is subjected to light-end distillation to form a crude acetic acid product stream comprising acetic acid and water, and an overhead stream comprising methyl iodide, water, methyl acetate, and acetic acid. The overhead stream is condensed in a decanter to produce a light, aqueous phase comprising water, acetic acid, and methyl acetate, and a heavy, organic phase comprising methyl iodide and methyl acetate. The heavy, organic phase is recycled to the carbonylation reactor. Methyl iodide is a catalyst promoter of the carbonylation and is expensive. Therefore, the decanter phase separation is a crucial step for the acetic acid production process.

U.S. Pat. No. 6,677,480 teaches a method which comprises measuring the density of the decanter heavy, organic phase and using the density to adjust the feed of methanol and to regulate the temperature in the reaction zone to optimize reactor conditions. However, the control scheme disclosed in this patent cannot effectively control the decanter phase separation because the decanter is three steps downstream of the reactor. Thus any changes in the reactor conditions in response to the density measurement of the decanter heavy, organic phase cannot effectively remedy the phase separation problem in the decanter because of the delayed measurement. In summary, new methods are needed for controlling the decanter phase separation of the acetic acid production process. Ideally, the new method allows controlling the decanter phase separation by measuring the composition of the reactor mixture, predicting its effect on the decanter phase separation, and then adjusting the reactor or the decanter conditions in response to the prediction.

SUMMARY OF THE INVENTION

Process for producing acetic acid by methanol carbonylation involves multiple steps, including reaction, flashing, light-ends distillation, phase separation, heavy-ends distillation, etc. The carbonylation reaction is performed by reacting methanol and carbon monoxide in the presence of a carbonylation catalyst, a catalyst stabilizer, methyl iodide, water and methyl acetate to produce an acetic acid stream comprising the catalyst, the catalyst stabilizer, methyl iodide, methyl acetate, water, acetic acid, and acetaldehyde. The acetic acid stream is flashed to produce a vapor stream comprising acetic acid, water, methyl acetate, and methyl iodide, and a liquid stream comprising the catalyst and the catalyst stabilizer. The vapor stream is subjected to light-end distillation to form a crude acetic acid product stream comprising acetic acid and water, and an overhead stream comprising methyl iodide, water, methyl acetate, and acetic acid. The overhead stream often contains byproducts of the carbonylation such as aldehydes and alkanes. The overhead stream is condensed in a decanter to produce a light, aqueous phase comprising water, acetic acid, methyl acetate, and aldehydes, and a heavy, organic phase comprising methyl iodide, methyl acetate and alkanes. The heavy, organic phase is recycled to the carbonylation reactor. The phase separation step is crucial because it ensures that methyl iodide is efficiently recycled. The invention provides a method which effectively controls phase separation of the decanter. The method comprises measuring the methyl acetate concentration in the reactor mixture, calculating the density of the heavy, organic phase of the decanter according to the measured methyl acetate concentration, and adjusting the conditions in the reactor or in the decanter in response to the measurement to ensure phase separation of the decanter. We found that the methyl acetate concentration in the reactor mixture directly responds to its concentration in the heavy, organic phase of the decanter, which, in turn, affects the density of the heavy, organic phase of the decanter and phase separation therein. The method of the invention provides a link between the decanter phase separation and the reactor conditions and therefore a timely adjustment of the reactor conditions can be made to endure phase separation of the decanter.

DETAILED DESCRIPTION OF THE INVENTION

The invention relates to a method for controlling phase separation in the decanter of an acetic acid production by methanol carbonylation. The carbonylation reaction is usually performed in the presence of a carbonylation catalyst and a catalyst stabilizer. Suitable carbonylation catalysts include those known in the acetic acid industry. Examples of suitable carbonylation catalysts include rhodium catalysts and iridium catalysts. Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_3$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates. The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are chloride-free such as acetates.

Preferably, the reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817, 869. Phosphine oxides are more preferred. Triphenylphosphine oxides are most preferred.

The carbonylation reaction is performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydroysis/methanolysis of polyvinyl acetate can be used for the carbonylation reaction.

Preferably, the reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the acetic reactor and then reacts with carbon monoxide and water to give acetic acid and regenerate the hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

An acetic acid product stream is withdrawn from the reactor and is separated, by a flash separation, into a liquid fraction comprising the catalyst and the catalyst stabilizer and a vapor fraction comprising the acetic acid product, the reactants, water, methyl iodide, and impurities generated during the carbonylation reaction including acetaldehyde. The liquid fraction is preferably recycled to the carbonylation reactor. The vapor fraction is then passed to a distillation column.

The distillation column, the so called "light ends distillation," separates an overhead comprising methyl iodide, water, methanol, methyl acetate, and acetaldehyde from an acetic acid stream comprising acetic acid, a small amount of water, and heavy impurities such as propionic acid. The acetic acid stream may be passed to a drying column to remove water and then be subjected to the so called "heavy ends distillation" to remove the heavy impurities.

The overhead from the light-ends distillation preferably comprises from about 60 wt % to about 90 wt % of methyl iodide, from about 5 wt % to about 15 wt % of methyl acetate, from about 1 wt % to about 10 wt % of acetic acid, 1 wt % or less of water, from about 1 wt % to about 10 wt % of alkanes, and about 2 wt % or less of acetaldehyde based on the total weight of the overhead.

The overhead is condensed and separated in a decanter to a light, aqueous phase and a heavy, organic phase. The heavy, organic phase comprises methyl iodide and the acetaldehyde. The light, aqueous phase comprises water, acetic acid, and methyl acetate. The aqueous phase is preferably recycled to the reactor or to the light ends distillation.

The method of the invention comprises measuring the methyl acetate concentration of the reactor mixture, calculating the density of the decanter heavy, organic phase according to the measured methyl acetate concentration, and adjusting the conditions in the reactor or in the decanter to ensure phase separation of the decanter. Any suitable methods for measuring the methyl acetate concentration can be used. Preferably, the methyl acetate concentration is measured by FTIR. Preferably, the methyl acetate concentration is measured by using an attenuated total reflectance (ATR) probe with a suitable crystal material. Transfer of light signal to the detector can be achieved by light pipe, chalcogenide fiber or other methods known to those skilled in the art of infrared spectroscopy. Using a similar analysis technique, this probe can optionally be inserted into the reactor or a reactor slipstream to provide online analysis capability. Alternately, a reactor slipstream is passed through an infrared analyzer equipped with either a flow through ATR cell or flow through transmission cell. Preferably, continuous flow is employed and reactor mixture is subsequently returned to the reaction system via the (low pressure) flash tank. By using a back pressure regulator or similar device located after solution has passed through the cells, essentially no pressure drop occurs across the cells. This ensures that analysis is performed with minimal change from the reactor pressure thereby resulting in no degassing or bubble formation in the cells. The temperature of the slipstream can be maintained anywhere between ambient and process temperature. Preferably, the temperature range is from 20° C. to 200° C. Optimal temperature is governed by several parameters, such as precipitation of solids, compatibility of cell window or crystal materials with process conditions, and controlling process reaction in the slipstream. More preferably, the temperature range of the slipstream is from 30° C. to 120° C. It is generally undesirable to operate at or below 30° C. as the reactor mixture shows increasing propensity to precipitate as temperature is lowered. It is also preferred to operate at or below 120° C. in order that reaction substantially quenches in the transfer lines, thus ensuring that the measured analyte concentrations are representative of the concentrations in the reactor immediately prior to sampling.

Depending on the temperature employed, the cell window or crystal material can be selected from materials including $CaF_2$, ZnS, sapphire, AMTIR (Se—Ge—As composite), Ge, ZnSe, Si, diamond, KRS-5 (thallium bromoiodide), and cubic zirconia. The nature of these materials in terms of composition, transmission ranges, and other properties are well known to those skilled in the art of spectroscopy and are readily available in spectroscopic and vendor literature. In a preferred embodiment of this invention, involving transmission cell analysis of a slipstream, sapphire windows are used. Sapphire has the appropriate transmission range to allow the analysis to be performed. It also displays good mechanical strength, chemical resistance and resistance to etching in the process described hereinabove.

Measuring can be carried out by analyzing in a combination of select spectral ranges of traditional mid (400 to 4000 $cm^{-1}$) and extended mid-(4000 to 7000 $cm^{-1}$) infrared regions. One option involves a dual transmission cell, dual detector setup in which reactor mixture sequentially flows through both cells. These cells differ only in path length. One cell has a path length of 0.05 to 0.15 mm which allows for analysis in the spectral region from 1800 to 5600 $cm^{-1}$ and thereby encompasses portions of traditional mid- and extended mid-infrared regions. The second cell has a path length of 0.2 to 3.0 mm which allows for analysis only in the extended mid-infrared region. The different cell path lengths are utilized to both counteract the highly absorbing nature of acetic acid and take advantage of the two different spectroscopic regions for reactant component characterization. Optionally, measuring of the methyl acetate concentration can be carried out using a single transmission cell, single detector setup. Depending on the cell path length chosen, different spectral regions can be used. A cell of path length 0.05 to 0.15 mm as described above allows quantization of all components absorbing in the spectral region from 1800-5600 $cm^{-1}$. This region is commonly referred to as the non fingerprint region and encompasses portion of both the traditional mid-infrared region and extended mid-infrared region as noted above. Alternately, a cell of much shorter path length, 0.005 to 0.015 mm allows access to both the non fingerprint region (1800 to 5600 $cm^{-1}$) and the fingerprint region, which is from 1800 to 400 $cm^{-1}$. This shorter path length can also be effectively achieved by using an ATR crystal rather than a transmission cell. As is known to those skilled in the art, utilization of a single cell or ATR crystal in analysis of the acetic acid reaction mixture involves accepting a compromise between the extent of the range of infrared spectrum analyzed and the quantitative accuracies of concentration of certain components in the mixture.

The method of the invention comprises calculating the density of the decanter heavy, organic phase based on the measured methyl acetate concentration of the reactor mixture. Preferably, the density, Z (g/mL), of the decanter heavy, organic phase is calculated based on the following equation:

$$Z = -0.082X - 0.023Y + 2.036$$

wherein X is the concentration of methyl acetate in the reactor mixture and Y is the alkanes concentration in the decanter heavy, organic phase. X and Y are measured by wt % based on the total weight of the reactor mixture or the decanter heavy, organic phase. The above equation is established by measuring samples of an acetic acid production process for values Z, X and Y and plotting the Z values against X values and Y values. The values Z are measured at ambient temperature (25° C. to 35° C.). The alkanes concentration Y can be measured by any suitable methods such as gas chromatography and FTIR. Unlike methyl acetate, which is an intermediate product of methanol carbonylation to acetic acid, alkanes are byproducts of the carbonylation. Alkanes concentration in the reactor mixture is usually very low and varies within a small range. However, alkanes may be concentrated in the decanter heavy, organic phase and affect phase separation because of its low density (about 0.75 g/mL). Therefore, a more convenient and accurate measurement of the alkanes concentration takes place in the decanter heavy, organic phase, although this invention does not exclude measuring the alkanes concentration in the reactor mixture and predicting its concentration in the decanter heavy, organic phase.

The method of the invention comprises adjusting the conditions in the reactor or in the decanter in response to the calculated density of the decanter heavy, organic phase so that phase separation occurs. Preferably, the decanter heavy, organic phase maintains a density within the range of 1.3 to 2.0 g/mL, more preferably within the range of 1.4 to 2.0 g/mL. When the calculated density is below this range, it means the methyl acetate concentration or the alkane concentration, or a combination of both, is too high because the densities of methyl acetate (0.9 g/mL) and alkanes (about 0.75 g/mL) are significantly lower than that of methyl iodide (2.3 g/mL). High concentration of methyl acetate in the decanter heavy, organic phase will lead to slow or incomplete phase separation in the decanter. Low decanter heavy, organic phase density will also impact the pumping ability of the heavy, organic phase pump which is often designed for a specific density range. High methyl acetate concentration in the reactor mixture indicates that the feed rate of methyl acetate is too high or the conversion rate of methyl acetate to acetic acid is too low. In this case, the methyl acetate feed rate can be reduced or the carbonylation reaction temperature can be increased to boost the conversion of methyl acetate to acetic acid. When the calculated density of the decanter heavy, organic phase is above the range, it often means that the methyl iodide concentration is too high. High methyl iodide concentration, although it favors the phase separation of the decanter, often indicates that methyl acetate in the reactor is insufficient. This insufficiency indicates that the methyl acetate feed is too slow and can be increased. Alternatively, the decanter condition can be adjusted in response to the calculated density of the decanter heavy, organic phase. For instance, if the calculated density of the decanter heavy, organic phase is too low, an additional amount of water can be added to the decanter to facilitate the phase separation. Also an additional amount of methyl iodide can be introduced into the decanter to facilitate the phase separation. There are many other ways to adjust the reactor condition or the decanter condition to ensure phase separation of the decanter.

The following example merely illustrates the invention. Those skilled in the art will recognize many variations that are within the spirit of the invention and scope of the claims.

Example 1

A continuous methanol carbonylation process is performed. The methyl acetate concentration in the reactor mixture is purposefully changed and the change of the decanter heavy, organic phase density is observed.

The methyl acetate concentration of the reactor mixture and the decanter heavy, organic phase density data are obtained for a period of 2.5 hours. The alkanes concentration of the decanter heavy, organic phase as measured by FTIR is found to be essentially unchanged (about 7.5 wt %) during the testing period. The heavy, organic phase density values are plotted against the methyl acetate concentration values and give an inverse linear correlation with an $R^2>0.99$. The resulting correlation equation is:

$$Z=-0.082X+1.865 \quad (1)$$

Z is decanter heavy, organic phase density and X is methyl acetate concentration of the reactor mixture.

As alkanes, in addition to methyl acetate, can also significantly impact decanter heavy, organic phase density, equation (1) is modified to include a term which quantitatively describes the effect of alkanes on heavy, organic phase density. This modification is based on the fact that alkanes ($C_6$ to $C_{14}$) typically observed in the process have a density of about 0.75 g/mL. In terms of decanter heavy, organic phase density, this corresponds to a drop in heavy, organic phase density of about 0.023 g/mL per wt % of alkanes in the heavy, organic phase. The modified equation which contains a term for heavy, organic phase alkanes concentration is:

$$Z=-0.082X-0.023Y+2.036 \quad (2)$$

Y is wt % alkanes in the heavy phase.

Equation (2) is applied to a commercial acetic acid production process. The concentration of alkanes in the decanter is about 10 wt %. Table 1 lists the methyl acetate concentration of the reactor mixture, the measured density of the decanter heavy, organic phase, and the calculated density of the decanter heavy, organic phase. The results in Table 1 indicate that the measured density and the calculated density of the decanter heavy, organic phase are very close to each other.

TABLE 1

EXPERIMENTAL RESULTS

| Time (minutes) | Methyl Acetate Concentration in Reactor Mixture, (wt %) | Decanter Heavy, Organic Phase Density, Cal. (g/mL) | Decanter Heavy, Organic Phase Density Measured (g/mL) |
|---|---|---|---|
| 0 | 3.94 | 1.483 | 1.467 |
| 30 | 3.98 | 1.480 | 1.472 |
| 40 | 4.00 | 1.478 | 1.484 |
| 90 | 3.96 | 1.481 | 1.476 |
| 145 | 4.02 | 1.476 | 1.480 |
| 195 | 4.35 | 1.449 | 1.484 |
| 225 | 4.62 | 1.427 | 1.480 |
| 275 | 4.82 | 1.411 | 1.450 |
| 300 | 4.11 | 1.469 | 1.428 |
| 330 | 3.82 | 1.493 | 1.411 |
| 360 | 3.47 | 1.521 | 1.430 |
| 390 | 3.87 | 1.489 | 1.481 |
| 430 | 3.81 | 1.494 | 1.508 |
| 460 | 3.61 | 1.510 | 1.523 |
| 520 | 3.55 | 1.515 | 1.525 |

We claim:

1. A method for controlling phase separation in a decanter of an acetic acid production process, said method comprising:

(a) measuring the methyl acetate concentration X (wt %) of a reactor mixture of the acetic acid production process;
   (b) calculating the density Z (g/mL) of a decanter heavy, organic phase according to the measured methyl acetate concentration wherein the calculation of the density of the decanter heavy, organic phase is based on the equation:

$$Z=-0.082X-0.023Y+2.036$$

wherein Y is the concentration (wt %) of alkanes in the decanter; and
   (c) adjusting the conditions in the reactor or in the decanter in response to the calculated density Z to control the phase separation in the decanter.

2. The method of claim 1, wherein the methyl acetate concentration of the reactor mixture is measured by FTIR.

3. The method of claim 1, wherein the density of the decanter heavy, organic phase is controlled within the range of 1.4 to 2.0 g/mL.

4. The method of claim 1, wherein the acetic acid production process comprises:

(i) reacting methanol and carbon monoxide in the presence of a carbonylation catalyst, a catalyst stabilizer, methyl iodide, water and methyl acetate to produce an acetic acid stream comprising the catalyst, the catalyst stabilizer, methyl iodide, methyl acetate, water, acetic acid, alkanes, and aldehydes;
   (ii) flashing at least a portion of the acetic acid stream to produce a vapor stream comprising acetic acid, water, methyl acetate, methyl iodide and acetaldehyde, and a liquid stream comprising the catalyst and the catalyst stabilizer;
   (iii) separating the vapor stream by distillation into an acetic acid product stream comprising acetic acid and water, and an overhead stream comprising methyl iodide, water, methyl acetate, acetic acid, and alkanes; and
   (iv) condensing the overhead stream in a decanter to produce a light, aqueous phase comprising water, acetic acid, and methyl acetate, and a heavy, organic phase comprising methyl iodide, methyl acetate, and alkanes.

5. The method of claim 4, wherein the catalyst is a rhodium catalyst.

6. The method of claim 4, wherein the catalyst stabilizer is selected from the group consisting of pentavalent Group VA oxides, metal iodide salts, and mixtures thereof.

7. The method of claim 6, wherein the catalyst stabilizer is a phosphine oxide.

8. The method of claim 7, wherein the catalyst stabilizer is triphenylphosphine oxide.

9. The method of claim 6, wherein the catalyst stabilizer is an alkali halide.

10. The method of claim 9, wherein the catalyst stabilizer is lithium iodide.

* * * * *